(12) United States Patent
Herold et al.

(10) Patent No.: US 12,357,495 B2
(45) Date of Patent: Jul. 15, 2025

(54) SENSOR PATCH FOR ATTACHMENT TO A BASE PLATE

(71) Applicant: Coloplast A/S, Humlebaek (DK)

(72) Inventors: Jakob Zeilberger Herold, Herlev (DK); Stine Renberg Andersen, Espergaerde (DK); Stephanie Knoedler, Nivaa (DK)

(73) Assignee: Coloplast A/S, Humlebaek (DK)

( * ) Notice: Subject to any disclaimer, the term of this patent is extended or adjusted under 35 U.S.C. 154(b) by 462 days.

(21) Appl. No.: 17/918,595

(22) PCT Filed: Apr. 14, 2021

(86) PCT No.: PCT/DK2021/050102
§ 371 (c)(1),
(2) Date: Oct. 13, 2022

(87) PCT Pub. No.: WO2021/209102
PCT Pub. Date: Oct. 21, 2021

(65) Prior Publication Data
US 2023/0141297 A1  May 11, 2023

(30) Foreign Application Priority Data
Apr. 14, 2020 (DK) .......................... PA 2020 70223

(51) Int. Cl.
*A61F 5/443* (2006.01)
*A61F 5/44* (2006.01)

(52) U.S. Cl.
CPC ............ *A61F 5/4404* (2013.01); *A61F 5/443* (2013.01)

(58) Field of Classification Search
CPC .............................. A61F 4/4404; A61F 5/443
See application file for complete search history.

(56) References Cited

U.S. PATENT DOCUMENTS

| | | | | |
|---|---|---|---|---|
| 10,500,084 B2* | 12/2019 | Hansen | .................... | A61F 5/445 |
| 10,799,385 B2* | 10/2020 | Hansen | .................... | G01M 3/40 |
| 11,547,596 B2* | 1/2023 | Hansen | .................... | A61F 5/44 |
| 11,559,423 B2* | 1/2023 | Speiermann | .......... | A61F 5/4404 |

(Continued)

FOREIGN PATENT DOCUMENTS

| | | |
|---|---|---|
| WO | 2007098762 A1 | 9/2007 |
| WO | 2019120448 A1 | 6/2019 |

(Continued)

*Primary Examiner* — Guy K Townsend
(74) *Attorney, Agent, or Firm* — Coloplast Corp., Coloplast A/S; Nick Baumann

(57) ABSTRACT

A sensor patch for attachment to a base plate for an ostomy appliance, the sensor patch having a distal side and an adhesive proximal side, the distal side being adapted for attachment to an adhesive surface of the base plate, wherein the adhesive surface of the base plate is adapted for attachment of the base plate to the skin surface of a user. The adhesive proximal surface of the sensor patch being provided with a release liner. The sensor patch comprises a central section and a peripheral section, where the central section is provided with a stomal opening comprising an inner edge portion encircling the stomal opening and where the inner edge portion of the release liner is provided with guiding means.

17 Claims, 3 Drawing Sheets

(56) References Cited

U.S. PATENT DOCUMENTS

| | | | | |
|---|---|---|---|---|
| 2016/0158056 A1* | 6/2016 | Davis | ............... | A61F 5/443 29/872 |
| 2019/0192334 A1* | 6/2019 | Hansen | ............... | A61F 5/445 |
| 2019/0247050 A1* | 8/2019 | Goldsmith | ............... | A61F 2/82 |
| 2020/0246175 A1* | 8/2020 | Hansen | ............... | G01M 3/16 |
| 2020/0246176 A1* | 8/2020 | Hansen | ............... | A61F 5/445 |
| 2020/0330258 A1* | 10/2020 | Hansen | ............... | A61F 13/511 |
| 2020/0337880 A1* | 10/2020 | Hansen | ............... | A61F 5/443 |
| 2020/0337881 A1* | 10/2020 | Hansen | ............... | A61F 5/4404 |
| 2020/0375499 A1* | 12/2020 | Hansen | ............... | A61B 5/4216 |
| 2020/0375784 A1* | 12/2020 | Hansen | ............... | A61F 5/443 |
| 2020/0383820 A1* | 12/2020 | Hansen | ............... | G16H 40/40 |
| 2020/0383821 A1* | 12/2020 | Hansen | ............... | A61F 5/443 |
| 2020/0390587 A1* | 12/2020 | Svanegaard | ............... | G16H 40/40 |
| 2020/0390589 A1* | 12/2020 | Hansen | ............... | A61F 5/443 |
| 2020/0395120 A1* | 12/2020 | Svanegaard | ............... | G06F 3/0482 |
| 2020/0405228 A1* | 12/2020 | Svanegaard | ............... | A61F 5/4404 |
| 2021/0000634 A1* | 1/2021 | Svanegaard | ............... | A61B 5/0004 |

FOREIGN PATENT DOCUMENTS

| | | | | |
|---|---|---|---|---|
| WO | WO-2019120451 A1 * | 6/2019 | ............... | A61F 5/44 |
| WO | 2020173534 A1 | 9/2020 | | |

* cited by examiner

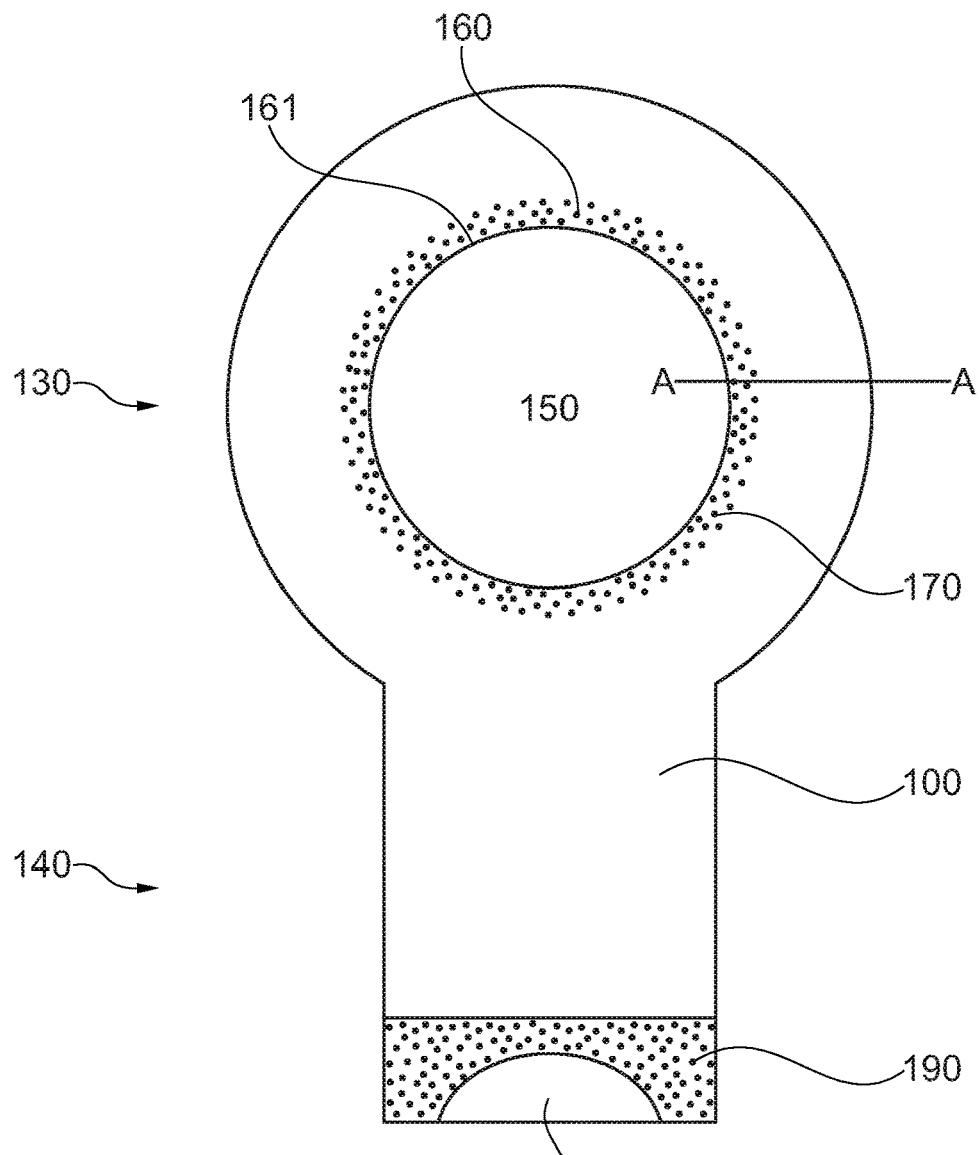
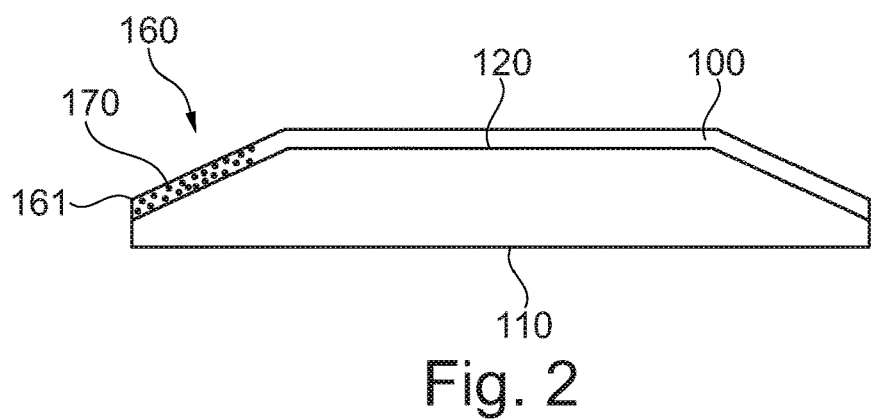

SENSOR PATCH FOR ATTACHMENT TO A BASE PLATE

The invention relates to a sensor patch for attachment to a base plate for an ostomy appliance and a method of attaching such sensor patch to an ostomy base plate.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general, safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY OF THE INVENTION

Disclosed is a sensor patch for attachment to a base plate for an ostomy appliance and a method for attaching such sensor patch to a base plate. The sensor patch has a proximal side and a distal side. The distal side is adapted for attachment to an adhesive surface of the base plate, and the adhesive surface of the base plate is adapted for attachment of the base plate to the skin surface of a user.

Also disclosed is a sensor patch for attachment to a base plate for an ostomy appliance, the sensor patch having a distal side and an adhesive proximal side, the distal side being adapted for attachment to an adhesive surface of the base plate, wherein the adhesive surface of the base plate is adapted for attachment of the base plate to the skin surface of a user, the adhesive proximal surface of the sensor patch being provided with a release liner, the sensor patch comprises a central section and a peripheral section, the central section is provided with a stomal opening comprising an inner edge portion encircling the stomal opening wherein the inner edge portion of the release liner is provided with guiding means.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 illustrates an embodiment of a sensor patch seen from the proximal side, FIG. 2 illustrates the embodiment of FIG. 1 in cross-section along the line A-A.

DETAILED DESCRIPTION

Figure 3:
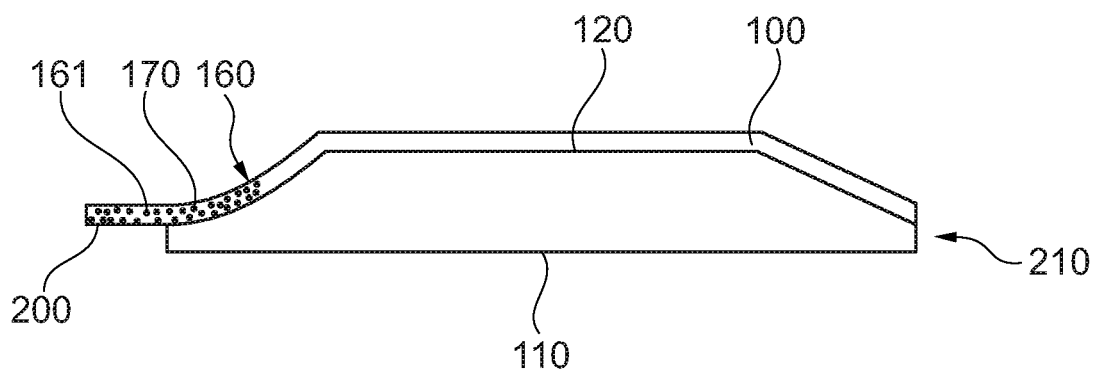
FIG. 3 illustrates an embodiment of a sensor patch in cross-section.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

Disclosed is a sensor patch for attachment to a base plate for an ostomy appliance. Such sensor patch facilitates detection of moisture propagation in the adhesive material provided for attaching the base plate to the skin surface of a user as well as detection of increased risk of leakage. For example, the sensor patch may allow electronic measurements of performance of the base plate and/or facilitate detection of increasing risks of leakage and/or facilitate detection of decreasing adherence of the base plate to the skin of the user.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate may comprise a first adhesive layer, i.e. a first layer of an adhesive material. During use, a proximal surface of the first adhesive layer adheres to the user's skin in the peristomal area and/or to additional seals, such as sealing paste, sealing tape and/or sealing ring. The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first adhesive layer may comprise a distal surface and a proximal surface. The distal surface of the first adhesive layer may be configured to face away from the skin of the user.

The first adhesive layer may form the adhesive surface of the base plate adapted for attachment of the base plate to the skin surface of the user. The first adhesive layer may form part of the adhesive surface of the base plate adapted for attachment of the base plate to the skin surface of the user.

The base plate may comprise a second adhesive layer, i.e. a second layer of an adhesive material, also denoted rim adhesive layer. The second adhesive layer may be of a different adhesive material than the first adhesive layer. The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second adhesive layer may comprise a distal surface and a proximal surface. The proximal surface of the second adhesive layer may be configured to adhere to the user's skin, e.g. at least at a rim portion of the second adhesive layer. The distal surface of the second adhesive layer may be configured to face away from the skin of the user. The second adhesive layer may be covering a larger area than the first adhesive layer, e.g. such that the proximal surface of the second adhesive layer forms an adhesive rim surrounding the first adhesive layer.

The sensor patch is adapted for attachment to the base plate. For example, the sensor patch may be configured to be positioned between the skin of the user and the proximal side of the base plate. For example, the sensor patch may be adapted for attachment to the first adhesive layer of the base plate. For example, a distal side of the sensor patch may be configured to be facing the proximal surface of the first adhesive layer of the base plate. For example, the sensor patch, such as a distal side of the sensor patch may be configured to adhere to the proximal surface of the first adhesive layer of the base plate.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch may comprise a sensor assembly. The sensor assembly may form a sensor assembly layer. The sensor assembly may have a distal side and a proximal side. The sensor patch may be configured to be positioned on the base plate such that the distal surface of the sensor assembly is coupled to the proximal adhesive surface of the base plate.

The sensor assembly may comprise a plurality of electrodes. The plurality of electrodes may include a first electrode and a second electrode for forming a first sensor. The plurality of electrodes may include a third electrode, a fourth electrode, a fifth electrode and/or a sixth electrode. The first electrode may be a common ground electrode. For example, a second sensor may be formed by the first electrode and the third electrode, a third sensor may be formed by the first electrode and the fourth electrode, a fourth electrode may be formed by the first electrode and the fifth electrode, and/or a fifth electrode may be formed by the first electrode and the sixth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enables electrode arrangement in few or a single electrode layer.

The sensor assembly may comprise a support layer, e.g. with a proximal surface and a distal surface. The plurality of electrodes may be provided, such as formed, on the proximal surface of the support layer, e.g. the plurality of electrodes may be positioned on the proximal surface of the support layer.

The sensor assembly may comprise a masking element, e.g. with a proximal surface and a distal surface. The masking element may be configured to electrically insulate at least parts of the plurality of electrodes from proximal layers, such as a first adhesive sensor layer. The masking element may cover or overlap parts of the plurality electrodes, e.g. when seen in the axial direction.

The sensor patch may comprise a first adhesive sensor layer, e.g. with a proximal side and a distal side. The first adhesive sensor layer may be arranged on a proximal side of the sensor assembly. The first adhesive sensor layer, such as the proximal side of the first adhesive sensor layer, may form the proximal side of the sensor patch. The proximal side of the first adhesive sensor layer may be configured to adhere to the user's skin. Thus, after being applied to the base plate, the combined base plate and sensor patch may form an adhesive proximal surface configured to be applied to the skin surface of the user. The first adhesive sensor layer may be made of a first adhesive sensor material, such as the first composition, the second composition or a third composition. The third composition may comprise one or more polyisobutenes and/or styrene-isoprene-styrene.

The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids.

The sensor patch is adapted to form a stomal opening with a centre point. The stomal opening is configured to allow passage of output through the stomal opening and into an ostomy pouch attached to the base plate.

Arranging the sensor patch correctly on the base plate can be difficult for the user. The sensor patch should be oriented correctly, with the distal side facing the base plate and the proximal side facing the skin of the user. If the sensor is applied wrongly, with the distal side facing the skin, several problems may arise. The sensors will not work properly as they do not contact the skin surface the way they are configured to, and the base plate may not adhere properly to the skin as the distal side of the sensor patch may not comprise the same adhesive properties as the proximal side—or it may even be non-adhesive. This may result in undesired leakage.

As the sensor patch may allow electronic measurements of performance of the base plate and/or to facilitate detection of increasing risks of leakage and/or to facilitate detection of decreasing adherence of the base plate to the skin of the user, the sensor patch should be oriented correctly. Electrodes need to be positioned correctly in order to perform its function and if the sensor patch may be oriented wrongly, then for example the electrodes may be embedded in adhesive instead of being in contact with the skin which evidently will lead to false measurements.

A sensor patch as disclosed herein and having guiding means on the release liner alleviates or minimises the problems mentioned above, because the user is guided to position the sensor patch correctly on the base plate.

The sensor patch comprises a central section and a peripheral section, the central section is provided with a stomal opening. When the sensor patch is applied to a base plate, the stomal opening may be arranged substantially concentric to a stomal opening in the base plate, the opening being accommodated for receiving a stoma. In embodiments, the central section has a substantially circular or oval shape.

In embodiments, the peripheral section is extending radially away from the central section. The peripheral section may encircle the central section, or it may extend radially outwards, in one or more directions, from the central section. In embodiments, the peripheral section comprises an elongated shape and extends radially outwards in one direction from the central section. The peripheral section may extend further than the outer rim of the base plate when the sensor patch is applied to such base plate, thereby leaving a part of the peripheral section unattached to the base plate.

In embodiments, the central section comprises a first adhesive and the peripheral section comprises a second adhesive. In embodiments, the first adhesive and the second adhesive are the same adhesive. In embodiments the first adhesive and the second adhesive have different properties. For example, the adhesives may differ with respect to adhesive tack and/or softness.

In aspects, a sensor patch where the release liners guide the user to apply the sensor patch correctly to the base plate is provided.

The adhesive proximal surface of the sensor patch is provided with a release liner and the sensor patch comprises a central section and a peripheral section, wherein the central section provided with a central section of the release liner and the peripheral section is provided with a peripheral portion of the release liner. The central section is provided with a stomal opening comprising an inner edge portion encircling the stomal opening and the release liner of the central section may have an inner edge portion encircling the stomal opening.

Embodiments relate to a sensor patch for attachment to a base plate for an ostomy appliance, the sensor patch having a distal side and an adhesive proximal side, the distal side being adapted for attachment to an adhesive surface of the base plate, wherein the adhesive surface of the base plate is adapted for attachment of the base plate to the skin surface of a user, the adhesive proximal surface of the sensor patch being provided with a release liner, the release liner comprising a central portion with an outer and inner edge portion and a peripheral portion, the sensor patch comprises a central section and a peripheral section, the central section is provided with a stomal opening comprising an inner edge portion encircling the stomal opening, wherein the inner edge portion of the release liner is provided with guiding means.

In embodiments, the guiding means are visual means. In embodiments, the guiding means are in the form of colour markings attracting the attention of the user to focus on the coloured area. A colour being distinctly different from the colour of the neighbouring part of the release liner may nudge the user to apply more attention to the selected area. In embodiments, the guiding means comprises one or more colour markings. The colour may be solid or in a pattern.

The guiding means serves two purposes: firstly, showing the user the area that needs special attention i.e. where to apply pressure and secondly, the guiding means may help the user to ensure the correct orientation of the sensor patch during applying the patch to the base plate.

In embodiments, the inner edge portion of the sensor patch is bevelled. The bevelling ensures smooth transition to the adhesive surface of the base plate and thereby avoiding an edge or groove that may give rise to leakage.

In embodiments, the guiding means are tactile means. By tactile is meant that the means can be sensed by touching the means. In embodiments, such tactile means may be dynamic in the sense that it comprises a material that can be flattened, collapsed or displaced when exposed to an impact. In embodiments, the guiding means comprises bubbles that can be collapsed when exposed to pressure, e.g. from a finger. The tactile means may be advantageous in the case where it is difficult for the user to observe the sensor patch and the base plate during application, for example using a one-piece device or in the case of obesity. The direct feedback may be an easy and informative way to let the user know, where the applied pressure and thereby the application of the sensor patch is (in)sufficient.

In embodiments, the tactile means may be static in the sense that they do not change conformation due to impact but stay in a specific conformation. In embodiments, the guiding means comprises a smoother surface than the rest of the release liner, compared to the neighbouring part of release liner. By smoother is meant that the surface of the release liner at the guide provides low resistance to a finger sliding over it. This may nudge the user to drive the finger along a smooth path, being intuitive to enter.

In embodiments, the guiding means comprises one or more embossed zones. In embodiments, the guiding means comprises a plurality of embossed zones.

In embodiments, the guiding means comprises a rougher surface than the neighbouring part of the release liner. By rougher is meant the surface of the release liner at the guide provides high resistance to a finger sliding over it, such as a ruffled surface that may encourage the user to apply extra pressure.

In embodiments, the guiding means comprises a smooth surface to which the finger will easily slide on or the guiding means may define a groove to fit the finger into or a combination of both features.

In embodiments, the guiding means are accessible or visual only from the proximal side of the sensor patch. Thereby the user is encouraged to have the correct orientation of the sensor patch.

In embodiments, the guiding means are configured for nudging the user to enter correct orientation of the sensor patch when attaching it to the base plate. In embodiments, the guiding means may be configured to nudge the user to access the area of the release liner and for example apply pressure to the area thereby securing the sensor patch to the base plate.

In embodiments, the inner edge portion of the release liner extends further inwards against a centre of the stomal opening to define an inner rim that is not supported by the adhesive sensor layer. In this way, the portion of the release liner not being supported by the sensor patch may protect the adhesive surface of the base plate from unintentional touching during the application of the sensor patch. In embodiments, the central portion of the release liner extends over the entire stomal opening.

In embodiments, the distal side of the sensor patch is non-adhesive. In embodiments, the sensor patch may be provided with a top film on the distal side. As the sensor patch is adhered to the base plate by the adhesive surface of the base plate, no adhesive is needed. Furthermore, in the case that the sensor patch is extending further than the base plate, a non-adhesive distal side may be advantageous in order not to stick to the clothes of the user.

In embodiments, the release liner is non-adhesive and can be releasably attached to the proximal adhesive surface of the sensor patch. In embodiments, the release liner is provided with a non-stick surface (siliconized) facing the sensor patch.

Embodiments relate to a method of attaching a sensor patch to an ostomy base plate comprising the steps of:
a. providing an ostomy base plate with a skin-facing adhesive surface,
b. providing a sensor patch as described above,
c. orienting the sensor patch with the proximal side facing away from the adhesive surface of the base plate,
d. attaching the distal surface of the sensor patch to the adhesive surface of the base plate, while being guided by the guiding means,
e. applying pressure along the guiding means at the inner edge portion of the release liner.

In embodiments, the method further comprises the step of removing the second release liner after application to the base plate.

Then the base plate with the applied sensor patch can be applied to the skin around a stoma of a patient.

Embodiments, and features of the various exemplary embodiments described in this application, may be combined with each other ("mixed and matched"), unless specifically noted otherwise.

DETAILED DESCRIPTION OF THE DRAWING

FIG. 1 shows an embodiment of a sensor patch seen from the proximal side. The proximal adhesive side of the sensor patch is covered by a first release liner (100) optionally covering the entire proximal adhesive side (120). The sensor patch comprises a central section (130) and a peripheral section (140), the central section (130) is provided with a stomal opening (150) comprising an inner edge portion (160) encircling the stomal opening (150). The release liner is also provided with an inner edge portion (161) and the inner edge portion (161) of the release liner is provided with guiding means (170). The peripheral section (140) of the release liner (100) may comprise a cut-out or a tab member for easy detachment of the release liner (100). The area nearby the tab/cut-out may be provided with visible means such as a colour to define a touch point (190) thereby nudging the user to attend this part when the release liner (100) is to be removed.

In FIG. 2 is shown the embodiment of FIG. 1 in cross-section along the A-A line. The sensor patch comprises a distal side (110) and a proximal adhesive side (120), the proximal adhesive side (120) of the sensor patch is covered by a first release liner (100). The distal side (110) being adapted for attachment to an adhesive surface of a base plate, the adhesive surface of the base plate being adapted for attachment of the base plate to the skin surface of a user. The guiding means (170) are provided on the inner edge portion (161) of the release liner (100). The guiding means (170) may be in the form of a visible means such as colour markings or it may be in the form of tactile means or a combination of visible and tactile means.

In FIG. 3 is shown a cross-section of an embodiment of the sensor patch, where the inner edge portion (161) of the release liner (100) extends further inwards against the centre of the stomal opening (150) to define an inner rim (200) that is not supported by the proximal adhesive surface of the sensor patch. In this way, the inner rim (200) of the release liner (100) not being supported by the sensor patch may protect the adhesive surface of the base plate from unintentional touching during the application of the sensor patch.

Figure 4:
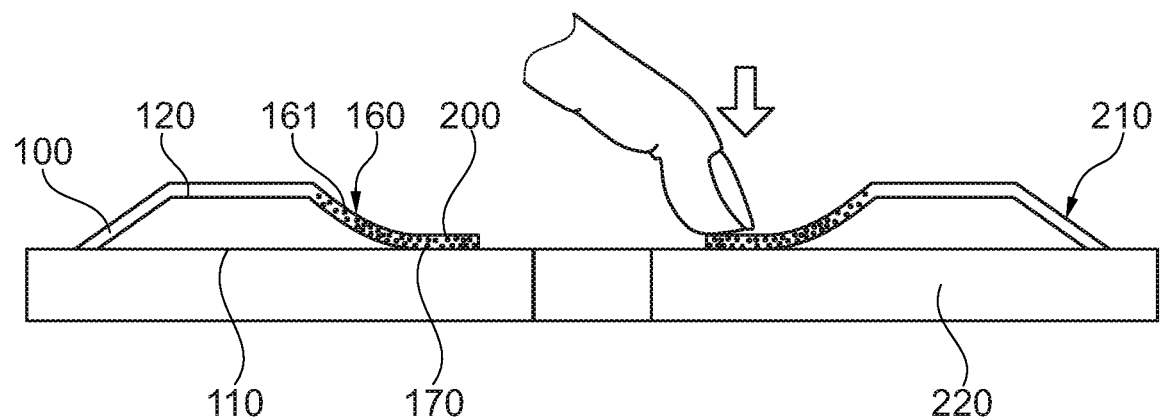
FIG. 4 illustrates the embodiment of a sensor patch shown in FIG. 3 mounted on a base plate, in cross-section.

In FIG. 4 is shown the sensor patch of FIG. 3 applied to a base plate (220), with a finger applying pressure to the guiding means in order to secure good adhesion of the inner edge portion (160, 200) of the sensor patch to the base plate (220).

Figure 5:
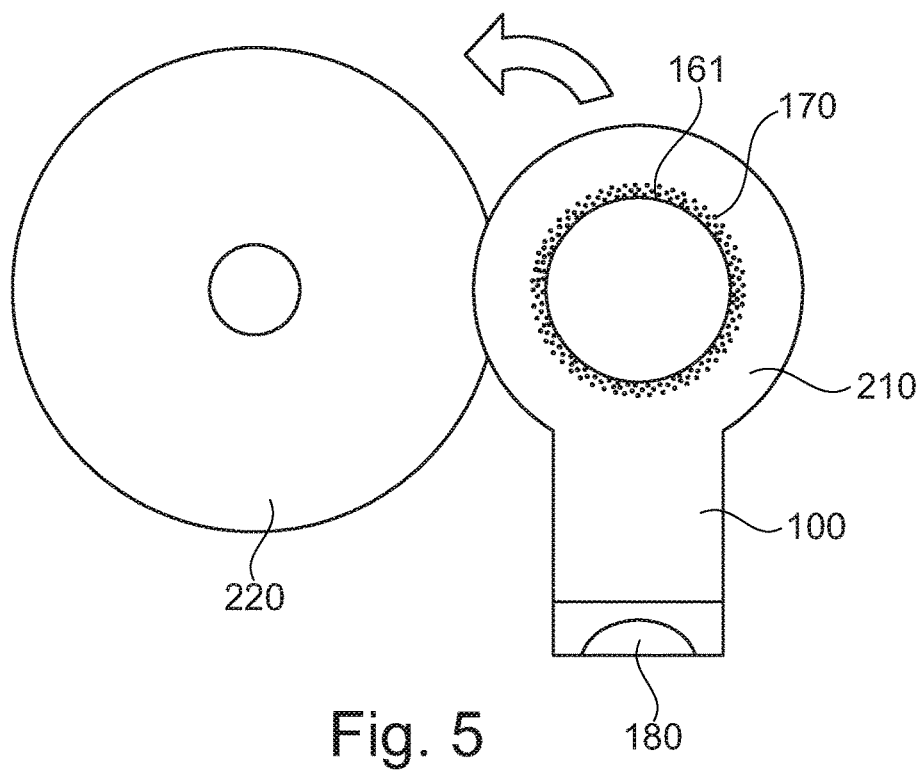
FIG. 5 and FIG. 6 illustrate an embodiment of a sensor patch being applied to a base plate, seen from proximal side.
Figure 6:
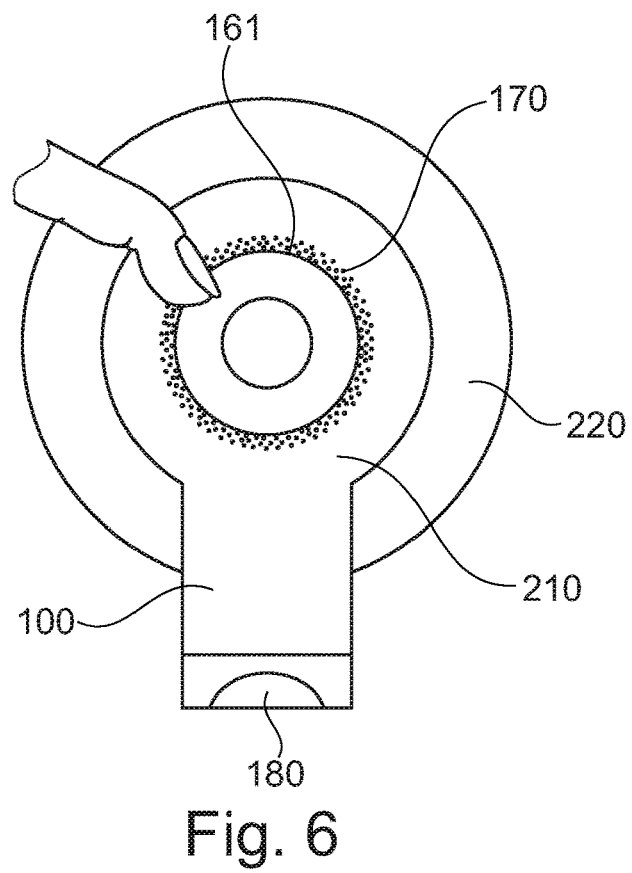

In FIG. 5 and FIG. 6 are shown application of a sensor patch (210) to a base plate (220), both seen from the proximal side. The sensor patch (210) is oriented with the guiding means (170) accessible from the proximal side, thereby ensuring correct orientation of the sensor patch (210) during application to the base plate (220). The sensor patch (210) is then combined with the base plate (220) as shown in FIG. 5 and pressure is applied with a finger to the guiding means (170) to ensure correct adhesion. Then the release liner (100) can subsequently be removed. Now the base plate (220) with the attached sensor patch (210) is ready to be applied to the skin around a stoma of a user.

The invention claimed is:

1. A sensor patch provided separately from and attachable to a base plate of an ostomy appliance, the sensor patch comprising:
   a distal side and an adhesive proximal side, the distal side of the sensor patch adapted for attachment to a first portion of an adhesive surface of the base plate, where a different second portion of the adhesive surface of the base plate is adapted for attachment of the base plate to skin of a user; and
   a release liner disposed on and covering the adhesive proximal side of the sensor patch;
   wherein the release liner comprises a central portion having a stomal opening defined by a release liner inner edge portion;
   wherein the release liner inner edge portion is provided with a guide located only on the proximal side of the sensor patch;
   wherein the guide assists the user in applying pressure along the release liner inner edge portion for attachment of the sensor patch to the first portion of the adhesive surface of the base plate;
   wherein, upon removal of the release liner from the sensor patch, the adhesive proximal side of the sensor patch and the different second portion of the adhesive surface of the base plate are attachable to the skin of the user.

2. The sensor patch of claim 1, wherein the guide assists the user in orienting the central portion and the stomal opening of the release liner relative to the stoma-receiving hole of the base plate of the ostomy appliance.

3. The sensor patch of claim 1, wherein the guide of the release liner comprises a smoother surface than a surface of a neighbouring part of the release liner.

4. The sensor patch of claim 1, wherein the guide of the release liner comprises a plurality of embossed zones.

5. The sensor patch of claim 1, wherein the guide of the release liner comprises a rougher surface than a surface of a neighbouring part of the release liner.

6. The sensor patch of claim 1, wherein the guide of the release liner comprises bubbles that collapse when pressed.

7. The sensor patch of claim 1, wherein the guide of the release liner comprises a color that is different from a colour of a neighbouring part of the release liner.

8. The sensor patch of claim 1, wherein, when the release liner is disposed on the sensor patch, the inner edge portion of the release liner extends inwards to over-hang the stomal opening of the sensor patch.

9. The sensor patch of claim 1, wherein the distal side of the sensor patch is non-adhesive.

10. The sensor patch of claim 1, wherein adhesive proximal side of the sensor patch is a circular portion and the sensor patch further comprises a peripheral portion extending radially away from the circular portion.

11. The sensor patch of claim 1, wherein the guide assists the user in applying pressure along the release liner inner edge portion for attachment of a perimeter of the stomal opening of the sensor patch around a stoma hole formed in the base plate.

12. The sensor patch of claim 1, further comprising an electrode adapted to electrically measure a performance of the base plate.

13. The sensor patch of claim 1, further comprising an electrode adapted to detect leakage of stomal liquid relative to the base plate.

14. The sensor patch of claim 1, further comprising an electrode adapted to detect a decrease in adherence between the adhesive surface of the base plate and the skin of the user.

15. A sensor patch provided separate from and attachable to a base plate of an ostomy appliance, the sensor patch comprising:
  a distal side and an adhesive proximal side, the distal side of the sensor patch adapted for attachment to a first portion of an adhesive surface of the base plate, where a different second portion of the adhesive surface of the base plate is adapted for attachment of the base plate to skin of a user;
  a stomal-receiving hole formed through the sensor patch; and
  a release liner disposed around the stomal-receiving hole of the sensor patch and covering the adhesive proximal side of the sensor patch;
  wherein the release liner comprises a first portion provided with a stoma opening defined by a release liner inner edge portion, with the stoma opening of the release liner axially aligned with the stomal-receiving hole formed through the sensor patch;
  wherein the release liner inner edge portion comprises a guide provided only on the proximal side of the sensor patch;
  wherein the guide assists the user in adhesively attaching a perimeter of the stomal-receiving hole formed through the sensor patch to the base plate of the ostomy appliance;
  wherein, upon removal of the release liner from the sensor patch, the adhesive proximal side of the sensor patch and the different second portion of the adhesive surface of the base plate are available for attachment to the skin of the user.

16. The sensor patch of claim 15, further comprising an electrode adapted to electrically measure a performance of the base plate.

17. The sensor patch of claim 15, further comprising an electrode adapted to detect leakage of stomal liquid relative to the base plate.

* * * * *